(12) United States Patent
Beckman et al.

(10) Patent No.: US 7,135,598 B2
(45) Date of Patent: Nov. 14, 2006

(54) N-VINYLFORMAMIDE DERIVATIVES, POLYMERS FORMED THEREFROM AND SYNTHESIS THEREOF

(75) Inventors: Eric J. Beckman, Aspinwall, PA (US); Toby M. Chapman, Pittsburgh, PA (US); Lianjun Shi, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 10/656,706

(22) Filed: Sep. 5, 2003

(65) Prior Publication Data

US 2004/0167338 A1    Aug. 26, 2004

Related U.S. Application Data

(60) Provisional application No. 60/484,948, filed on Jul. 3, 2003, provisional application No. 60/408,730, filed on Sep. 6, 2002.

(51) Int. Cl.
    *C07C 233/03* (2006.01)
(52) U.S. Cl. .................................... 564/215
(58) Field of Classification Search ................ 564/215
    See application file for complete search history.

(56) References Cited

U.S. PATENT DOCUMENTS

| | | | |
|---|---|---|---|
| 4,444,667 A | | 4/1984 | Burkert |
| 4,942,259 A | * | 7/1990 | Parris et al. ................ 564/187 |
| 5,059,713 A | * | 10/1991 | Armor et al. ............... 564/187 |
| 5,262,008 A | | 11/1993 | Moench |
| 5,463,110 A | | 10/1995 | Chen |
| 5,777,121 A | | 7/1998 | Curran |
| 5,859,247 A | | 1/1999 | Curran |
| 6,156,896 A | | 12/2000 | Curran |
| 6,727,390 B1 | | 4/2004 | Curran |
| 6,734,318 B1 | | 5/2004 | Curran |
| 6,749,756 B1 | | 6/2004 | Curran |
| 6,825,043 B1 | | 11/2004 | Curran |
| 6,861,544 B1 | | 3/2005 | Curran |
| 6,897,331 B1 | | 5/2005 | Curran |

FOREIGN PATENT DOCUMENTS

| | | |
|---|---|---|
| EP | 0 763 522 | 3/1997 |
| EP | 0 816 351 | 1/1998 |
| NL | 6526959 | 6/1966 |
| WO | WO 2004/02252 | 3/2004 |

OTHER PUBLICATIONS

Kless et al., Organometallics, vol. 16, 2096-2100, 1997.*
6526956, 1964, NLX, Hoechst AG, Abstract.
Pinschmitdt, R.K., Jr. et al.; "New N-Vinylformamide Derivatives as reactive Monomers and Polymers"; Chemical Abstract Service, Columbus, Ohio, 2000, 119-131.

Ishibashi, Hiroyuki et. al.; "6-Endo-Trig and 5-Exo-Trig Selective Aryl Radical Cyclizations of N-(o-Bromobenzyl) Enamides"; Chemical Abstract Service, Columbus, Ohio, 2000; 16; 1527-1528.
Meuzelaar, Gerrit J. et. al.; "Synthesis of Gama-Unsaturated Enamides by N-Acylation of Imines Derived from Gamma-Unsaturated Amines" Chemical Abstracts Service, Columbus, Ohio, US; 1997; 6; 1159-1163.
Badesso, R.J. et. al.; "Synthesis of Amine Functional Homopolymers with N-Ethenylformamide"; Glass, E.; Ed.; America Chemcial Society, 1995, 489-504.
Pinschmidt, Jr. R.K. et. al.; "Amine Functional Polymers Based on N-Ethenylformamide"; Progress in Organic. Coatings, 1996, 27 209-218.
Pinschmidt, Jr. R.K. et al.; "N-Vinylformamide Derivatives and Their Use in Radiation Cure Coatings" Polym. Preprint. 1998, 39, 639-642.
Kurtz, P. et.al.; "Enamide"; Liebigs Ann. Chem., 1972, 764, 69-93.

(Continued)

*Primary Examiner*—Shailendra Kumar
(74) *Attorney, Agent, or Firm*—Bartony & Hare, LLP

(57) ABSTRACT

A method of synthesizing a compound having the formula:

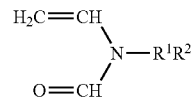

comprising the step of:
reacting a N-vinylformamide salt having the formula

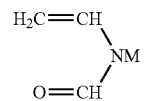

with a compound having the formula $XR^1R^2$; wherein X is Br, Cl or I, M is an alkali metal or an alkali earth metal, $R^1$ is a C0–C25 alkylene group, a C0–C25 fluroalkylene group or a C0–C25 perfluoro alkylene group, $R^2$ is H, provided $R^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —$OR^3$, wherein, $R^3$ is an alkyl group, a fluoroalkyl group, a perfluoroalkyl group, or an aryl group, —$C(O)R^4$, —$C(O)OR^4$, —$OC(O)R^4$, —$OC(O)R^4$, wherein $R^4$ is an H, an alkyl group, a fluoroalkyl group, a perfluoroalkyl group, or an aryl group, a phthalimide group or $NR^5 R^5$ wherein $R^5$ and $R^5$ are independently H, —$C(O)R^4$, an alkyl, a fluoroalkyl group, a perfluoroalkyl group or an aryl group.

10 Claims, 3 Drawing Sheets

OTHER PUBLICATIONS

Sheehan, J.C. and Yang, D.-D. H.; "The Use of N-Formylamino Acids in Peptide Synthesis"; Journal Am. Chem. Soc. 1958, 80, 1154-1158.

Pinschmidt, Jr. R.K. et. al.; "N-Vinylformamide-Building Block for Novel Polymer Structures"; J.Macromol Sci.Pure Appl. Chem., 1997, A34(10), 1885-1905.

Mohamadi, F. et. al.; "MacroModel—An Integrated Software System for Modeling Organic and Bioorganic Molecules Using Molecular Mechanics"; Comput. Chem. 1990, 11, 440-467.

Bourn, A. J. R. et al.; "Cis-Trans Isomerism in N-Methyl and N-Ethylformanilide"; Tetrahedron, 1966, 22, 1825-1829.

Eliel, E. L. et. al.; "Stereochemistry of Organic Compounds", Wiley, New York, 1994, 696-697.

Gu, L. et.al.; "Kinetics and Modeling of Free Radical Polymerization of N-Vinylformamide", Polymer 2001, 42, 3077-3086.

Gu, L. et.al.; "The Nature of Crosslinking in N-Vinylformamide Free-Radical Polymerization"; Macromol. Rapid Commun. 2001, 22, 212-214.

Chujo, Y. et.al.; "Molecular Design of Interfacially Active Graft Copolymers by Macromonomer Method"; Polym. J. 1985, 17, No. 1, 133-141.

Lucas, E.F. et.al.; "Surface Properties of Graft Copolymers Surfactants: Behavior at the Water/Toluene Interface", J. Appl. Polym. Sci. 1992, 46, 733-737.

Buszello, K. et.al.; "Pharmaceutical Emulsions and Suspensions"; Nielloud, F. and Marti-Mestres, G., Eds., Marcel Dekker, Inc., New York, 2000, Ch. 5, 195-197.

Liu, F. et.al.; "Amphipathic Polyethylene Glycol Stabilized Emulsions (o/w): Physical Characterization and in vivio Distribution", International Journal of Pharmaceutics, 1995, 125, 73-80.

Qiu, Y. et.al.; "Novel Nonionic Oligosaccharide Surfactant Polymers Derived From Poly (vinylamine) With Pendant Dextran and Hexanoyl Groups", Macromolecules 1998, 31, 165-171.

Meuzelaar, Gerrit J. et.al.; Abstract. Beilstein Institut Zur Foerderung der Chemischen Wissenschaften, Frankfurt am Main, Ge, vol. 6, 1997, pp. 1159-1164.

Kurtz, P. et.al.; Abstract. Beilstein Institut Zur Foerderung der Chemischen Wissenschaften, Frankfurt am Main, Ge, vol. 764, 1972, pp. 69-93.

Eberson, Lennart et.al.; Abstract. Beilstein Institut Zur Foerderung der Chemischen Wissenschaften, Frankfurt am Main, Ge, vol. 38, No. 5, 1984, pp. 345-350.

Ishibashi, Hiroyuki et.al.; Abstract. Beilstein Institut Zur Foerderung der Chemischen Wissenschaften, Frankfurt am Main, Ge, vol. 16, 2000, pp. 1527-1528.

Trofimou, B.A. et.al.; Abstract. Beilstein Institut Zur Foerderung der Chemischen Wissenschaften, Frankfurt am Main, Ge, 1981, pp. 1405-1409.

Kleiner H. J. et.al.; Abstract. Beilstein Institut Zur Foerderung der Chemischen Wissenschaften, Frankfurt am Main, Ge, 1974, pp. 751-764.

Ishibashi, Hiroyuki et. al.; "6-Endo-Trig and 5-Exo-Trig Selective Aryl Radical Cyclizations of N-(o-Bromobenzyl) Enamides"; Chemical Abstract Service, Columbus, Ohio, 2000; 16; 1527-1528.

\* cited by examiner

N-VINYLFORMAMIDE DERIVATIVES, POLYMERS FORMED THEREFROM AND SYNTHESIS THEREOF

CROSS-REFERENCE TO RELATED APPLICATIONS

The present application claims the benefit of U.S. Provisional Patent Application Ser. No. 60/408,730, filed Sep. 6, 2002 and U.S. Provisional Patent Application Ser. No. 60/484,948 filed Jul. 3, 2003 (Express Mail Label No. EL903258218US), the disclosures of which are incorporated herein by reference.

BACKGROUND OF THE INVENTION

The present invention relates to the N-vinylformamide derivative compounds, to polymers thereof and to the synthesis of N-vinylformamide derivative compounds and polymers thereof.

N-vinylformamide (NVF) is a monomer with potentially useful properties in that it free-radically polymerizes to produce water-soluble poly(N-vinylformamide) (PNVF) and also undergoes controlled radical polymerization using RAFT methodology. Badesso, R. J.; Nordquist, A. F.; Pinschmidt, Jr. R. K.; and Sagl, D. J. "Hydrophilic polymers: performance with Environmental Acceptance", Glass, E.; Ed.; America Chemical Society, Washington, D.C., 1995, p 489. PNVF is probably the most practical precursor for preparation of poly(vinylamine). In that regard, PNVF is easily hydrolyzed under basic or acidic conditions (see Scheme 1) to form poly(vinylamine).

Scheme 1

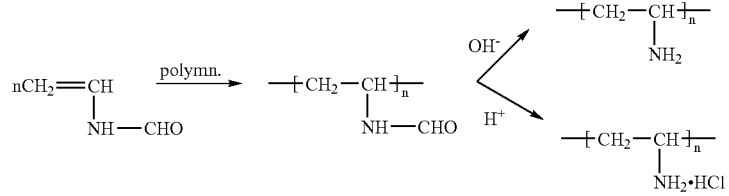

Copolymers of NVF with monomers such as styrene and methyl methacrylate have been generated and are reported to fit a broad range of commercial applications, including water treatment, coatings and paper manufacture. Pinschmidt, Jr. R. K.; Wasowski, L. A.; Orphanides, G. G.; Yacoub, K. Prog. Org. Coat. 1996, 27, 209; Burkert, H.; Brunnmuler, F.; Beyer, K.; Mkroner, M.; Muller, H. U.S. Pat. No. 4,444,667, 1984; Pinschimdt, Jr, R. K.; Chen, N. Polym. Prepr. 1998, 39, 639; Monech, D.; Hartmann, H.; Freudenberg, E.; Stange, A. U.S. Pat. No. 5,262,008, 1993.

NVF is also a multifunctional molecule. In addition to its C=C double bond for addition reactions or polymerization, NVF has a weakly acidic proton on the nitrogen flanked by the formyl and vinyl groups. NVF can thus act as a nucleophile.

A number of N-vinylformamide derivative monomers have been reported. For example, Kurtz, et al. described a process for preparing N-cyanoethyl-N-vinylformamide by the reaction of acrylonitrile and N-vinylformamide in benzene in the presence of potassium cyanide at room temperature. Kurtz, P.; Disselnkoetter, H. Liebigs Ann. 1972, 69–93, 764. Cramer et al. report a process for making N-methyl-N-vinylformamide by the reaction of methyl iodide and N-vinylformamide in the presence of 50% NaOH at room temperature. Cramer, J.; Dehmer, K.; Jensen, H.; Mitzlaff, M.; Pietsch, H.; Pistorius, R.; Schmidt, E. EP 19225, 1980.

Several additional synthetic routes for making N-vinylformamide derivative monomers have been reported. Pinschmidt, Jr., et al., for example, developed 3-(N-vinylformamido) propionates and 2-methyl-3-(N-vinylformamido) propionates by the Michael addition reaction of N-vinylformamide with acrylic or methacrylic acid esters using basic catalysts such as sodium methoxide, sodium hydride, or butyllithium. U.S. Pat. No. 5,463,110. Those monomers have been used in radical polymerizations or as components in photocurable coatings or crosslinking agents and chain extenders. Sugita et al. disclosed a process for making bifunctional crosslinking reagents such as N,N'-methylenebis(N-vinyl acetamide) including N,N'-methylenebis(N-vinylformamide)) by the reaction of N-vinylacetamide with dibromomethane at the room temperature. JP 03,227,310.

It is very desirable to develop new synthetic routes to existing and novel derivatives or analogs of N-vinylformamide as well as to develop new polymers synthesized from such compounds.

SUMMARY OF THE INVENTION

In one aspect, the present invention provides a method of synthesizing a compound having the formula:

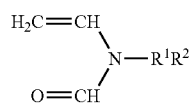

comprising the step of:

reacting a N-vinylformamide salt having the formula

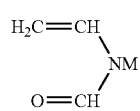

with a compound having the formula $XR^1R^2$ (for example, in the presence of a base); wherein X is Br, Cl or I, M is an alkali metal or an alkali earth metal, $R^1$ is a C0–C25 alkylene group, a C0–C25 fluroalkylene group or a C0–C25 perfluoro alkylene group, $R^2$ is H, provided $R^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —$OR^3$, wherein, $R^3$ is an alkyl group, a fluoroalkyl group, a perfluoroalkyl group, or an aryl group, —$C(O)R^4$, —$C(O)OR^4$, —$OC(O)R^4$, wherein $R^4$ is an H, an alkyl group, a fluoroalkyl group, a perfluoroalkyl group, or an aryl group, a phthalimide group or $NR^5R^5$ wherein $R^5$ and $R^5$ are independently H, —$C(O)R^4$, an alkyl, a fluoroalkyl group, a perfluoroalkyl group or an aryl group.

The N-vinylformamide salt can, for example, be formed by reacting an alkali metal base or an alkali earth metal base with N-vinylformamide. In one embodiment, the M is K or Na. The alkali metal base can, for example, be t-BuOK, wherein the resultant N-vinylformamide salt is N-vinylformamide potassium salt.

X is preferably Br. In several embodiments, $R^1$ is a C1–C10 alkylene group or a C1–C10 perfluoroalkylene group. In another embodiment, $R^2$ is a C1–C10 alkyl group or a C1–C10 perfluoroalkyl group. In still another embodiment, $R^2$ is a phthalimide group.

In another aspect, the present invention provides a method of synthesizing a copolymer comprising the step of reacting a compound having the formula:

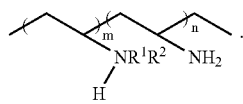

with at least one vinyl compound having at least one vinyl group (—CH=CH$_2$), wherein $R^1$ is a C0–C25 alkylene group, a C0–C25 fluroalkylene group or a C0–C25 perfluoro alkylene group, $R^2$ is H, provided $R^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —$OR^3$, wherein, $R^3$ is an alkyl group, a fluoroalkyl group, a perfluoroalkyl group, or an aryl group, —$C(O)R^4$, —$C(O)OR^4$, —$OC(O)R^4$, wherein $R^4$ is an H, an alkyl group, a fluoroalkyl group, a perfluoroalkyl group, or an aryl group, a phthalimide group or $NR^5R^5$ wherein $R^5$ and $R^5$ are independently H, —$C(O)R^4$, an alkyl, a fluoroalkyl group, a perfluoroalkyl group or an aryl group.

In one embodiment, the vinyl compound is N-vinylformamide. In other embodiments, the vinyl compound has the formula CH$_2$=CH—$R^6$, where $R^6$ is —OC(O)—CH$_3$ (vinyl acetate), —C(O)—O—$R^7$ (vinyl acrylates), wherein $R^7$ is an alkyl group, or —C(O)OH (acrylic acid). In one such embodiment, $R^7$ is a methyl group.

When the compound is reacted with NVF, the copolymer includes the following repeat units:

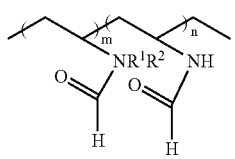

wherein m and n are integers.

The copolymer can be hydrolyzed to form a copolymer having the repeat units:

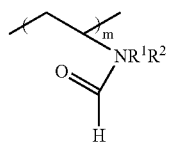

The hydrolysis can, for example, occur under basic conditions (for example, in aqueous NaOH) or under acidic conditions.

In still another aspect, the present invention provides a polymer having the formula:

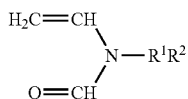

wherein m is an integer, $R^1$ is a C0–C25 alkylene group, a C0–C25 fluroalkylene group or a C0–C25 perfluoro alkylene group, $R^2$ is H, provided $R^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —$OR^3$, wherein, $R^3$ is an alkyl group, a fluoroalkyl group, a perfluoroalkyl group, or an aryl group, —$C(O)R^4$, —$C(O)OR^4$, —$OC(O)R^4$, wherein $R^4$ is an H, an alkyl group, a fluoroalkyl group, a perfluoroalkyl group, or an aryl group, a phthalimide group or $NR^5R^5$ wherein $R^5$ and $R^5$ are independently H, —$C(O)R^4$, an alkyl, a fluoroalkyl group, a perfluoroalkyl group or an aryl group.

In a further aspect, the present invention provides a copolymer produced by reaction of a compound having the formula:

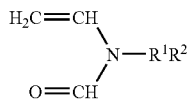

with N-vinylformamide, wherein the copolymer includes the following repeat units:

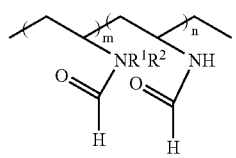

and wherein m and n are independently, integers, $R^1$ is a C0–C25 alkylene group, a C0–C25 fluroalkylene group or a C0–C25 perfluoro alkylene group, $R^2$ is H, provided $R^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —OR$^3$, wherein, R$^3$ is an alkyl group, a fluoroalkyl group, a perfluoroalkyl group, or an aryl group, —C(O)R$^4$, —C(O)OR$^4$, —OC(O)R$^4$, wherein R$^4$ is an H, an alkyl group, a fluoroalkyl group, a perfluoroalkyl group, or an aryl group, a phthalimide group or NR$^5$R$^5$ wherein R$^5$ and R$^5$ are independently H, —C(O)R$^4$, an alkyl, a fluoroalkyl group, a perfluoroalkyl group or an aryl group.

The copolymer can be hydrolyzed to from a copolymer with the repeat units:

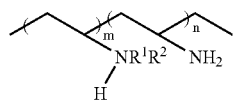

In another aspect, the present invention provides a polymer having the formula:

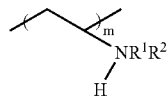

wherein m is an integer, R$^1$ is a C0–C25 alkylene group, a C0–C25 fluroalkylene group or a C0–C25 perfluoro alkylene group, R$^2$ is H, provided R$^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —OR$^3$, wherein, R$^3$ is an alkyl group, a fluoroalkyl group, a perfluoroalkyl group, or an aryl group, —C(O)R$^4$, —C(O)OR$^4$, —OC(O)R$^4$, wherein R$^4$ is an H, an alkyl group, a fluoroalkyl group, a perfluoroalkyl group, or an aryl group, a phthalimide group or NR$^5$R$^5$ wherein R$^5$ and R$^5$ are independently H, —C(O) R$^4$, an alkyl, a fluoroalkyl group, a perfluoroalkyl group or an aryl group.

In a further aspect, the present invention provides a polymer having the formula:

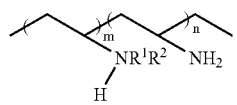

wherein m is an integer, R$^1$ is a C0–C25 alkylene group, a C0–C25 fluroalkylene group or a C0–C25 perfluoro alkylene group, R$^2$ is H, provided R$^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —OR$^3$, wherein, R$^3$ is an alkyl group, a fluoroalkyl group, a perfluoroalkyl group, or an aryl group, —C(O)R$^4$, —C(O)OR$^4$, —OC(O)R$^4$, wherein R$^4$ is an H, an alkyl group, a fluoroalkyl group, a perfluoroalkyl group, or an aryl group, a phthalimide group or NR$^5$R$^5$ wherein R$^5$ and R$^5$ are independently H, —C(O) R$^4$, an alkyl, a fluoroalkyl group, a perfluoroalkyl group or an aryl group, the polymer having end groups that are either.

In another aspect, the present invention provides a (for example, partially hydrolyzed), random copolymer including the following repeat units:

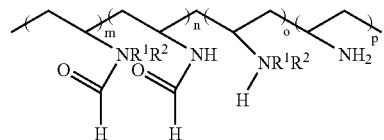

and wherein m, n, o and p are independently, integers, R$^1$ is a C0–C25 alkylene group, a C0–C25 fluroalkylene group or a C0–C25 perfluoro alkylene group, R$^2$ is H, provided R$^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —OR$^3$, wherein, R$^3$ is an alkyl group, a fluoroalkyl group, a perfluoroalkyl group, or an aryl group, —C(O)R$^4$, —C(O)OR$^4$, —OC(O)R$^4$, wherein R$^4$ is an H, an alkyl group, a fluoroalkyl group, a perfluoroalkyl group, or an aryl group, a phthalimide group or NR$^5$R$^5$ wherein R$^5$ and R$^5$ are independently H, —C(O)R$^4$, an alkyl, a fluoroalkyl group, a perfluoroalkyl group or an aryl group. One skilled in the art will recognize that the repeat units of the copolymer need not be arranged in a set manner.

In a further aspect, the present invention provides a (for example, partially hydrolyzed) polymer including the following repeat units:

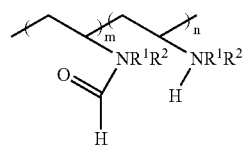

and wherein m and n are independently, integers, R$^1$ is a C0–C25 alkylene group, a C0–C25 fluroalkylene group or a C0–C25 perfluoro alkylene group, R$^2$ is H, provided R$^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —OR$^3$, wherein, R$^3$ is an alkyl group, a fluoroalkyl group, a perfluoroalkyl group, or an aryl group, —C(O)R$^4$, —C(O)OR$^4$, —OC(O)R$^4$, wherein R$^4$ is an H, an alkyl group, a fluoroalkyl group, a perfluoroalkyl group, or an aryl group, a phthalimide group or NR$^5$R$^5$ wherein R$^5$ and R$^5$ are independently H, —C(O)R$^4$, an alkyl, a fluoroalkyl group, a perfluoroalkyl group or an aryl group.

In still another aspect, the present invention provides a compound having the formula:

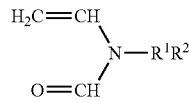

wherein R$^1$ is a C0–C25 alkylene group, a C0–C25 fluroalkylene group or a C0–C25 perfluoro alkylene group, R$^2$ is H, provided R$^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —OR$^3$, wherein, R$^3$ is an alkyl group, a fluoroalkyl group, a perfluoroalkyl group, or an aryl group, —C(O)R$^4$, —C(O)OR$^4$, —OC(O)R$^4$, wherein R$^4$ is an H, an alkyl group, a fluoroalkyl group, a perfluoroalkyl group, or an aryl group, a phthalimide group or NR$^5$R$^5$ wherein R$^5$ and R$^5$ are independently H, —C(O)R$^4$, an alkyl, a fluoroalkyl group, a perfluoroalkyl group or an aryl group.

In one embodiment, X is Br. In another embodiment, R$^1$ is a C1–C10 alkylene group or a C1–C10 perfluoroalkylene group. In another embodiment, R$^2$ is a C1–C10 alkyl group or a C1–C10 perfluoroalkyl group. R$^2$ in another embodiment is a phthalimide group.

The terms "alkyl", "aryl" and other groups refer generally to both unsubstituted and substituted groups unless specified to the contrary. Such groups can be substituted with a wide variety of substituents. Unless otherwise specified, alkyl groups are hydrocarbon groups and are preferably C1–C25 (that is, having 1 to 25 carbon atoms) alkyl groups, and more preferably C1–C10 alkyl groups, and can be branched or unbranched, acyclic or cyclic. The above definition of an alkyl group and other definitions apply also when the group is a substituent on another group. The term "fluoroalkyl group" refers to an alkyl group wherein at least one, but not all hydrogen atoms, are replaced by a fluorine atom. The term "perfluoroalkyl group: refers to an alkyl group in which all hydrogen atoms are replace by fluorine atoms. The term "aryl" refers preferably to phenyl or naphthyl. As used herein, the term vinyl group refers to the group $CH_2=CH-$.

The term "alkylene", refers to bivalent forms of alkyl groups as defined above. Alkylene groups (including fluroalkylene groups and perfluoroalkylene groups) are preferably C1–C25 alkylene groups, and more preferably C1–C10 alkylene groups. Most preferably, alkylene groups are C1–C5 alkylene groups.

The term "phthalimide group" refers to the group $C_6H_4(CO)_2N-$ or

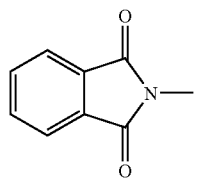

As used herein, the term "polymer" refers to a compound having multiple repeat units (or monomer units) and includes the term "oligomer," which is a polymer that has only a few repeat units. The term polymer also includes copolymers which is a polymer including two or more dissimilar repeat units (including terpolymers—comprising three dissimilar repeat units—etc.). One skilled in the art will recognize that the end groups of the polymers of the present invention will correspond to one of the monomers used to form the polymer. In the case of a partially hydrolyzed polymer of the present invention, the end group can be hydrolyzed or can be unhydrolyzed.

The present invention, along with the attributes and attendant advantages thereof, will best be appreciated and understood in view of the following detailed description taken in conjunction with the accompanying drawings.

DETAILED DESCRIPTION OF THE INVENTION

Figure 1:
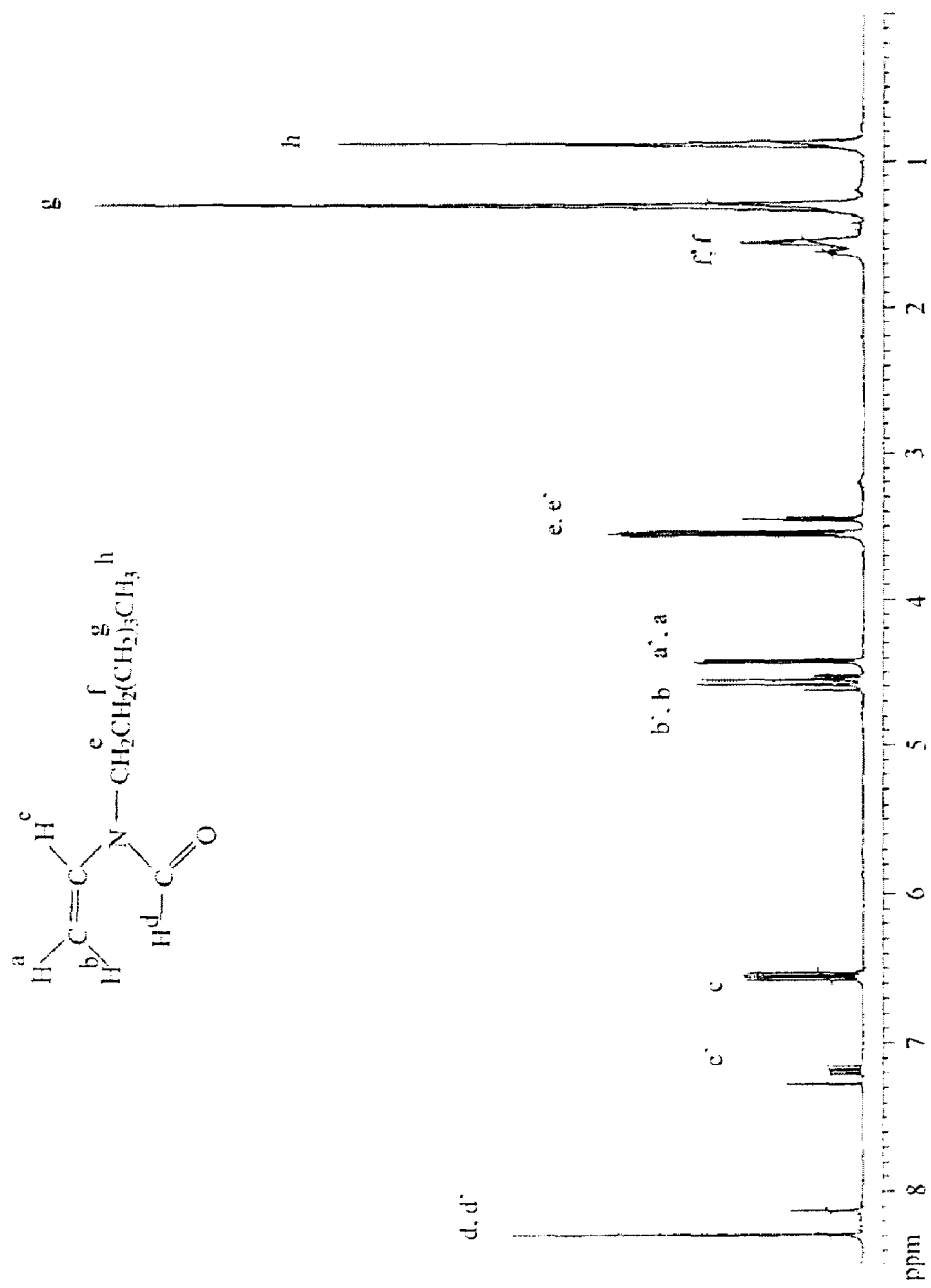
FIG. 1 illustrates an $^1$H-NMR spectrum of N-n-hexyl-N-vinylformamide.

In the general synthetic scheme for the synthesis of N-vinylformamide derivatives or analogs of the present invention, a salt of N-vinylformamide is reacted with a halogenated organic group as illustrated in Scheme 2A below.

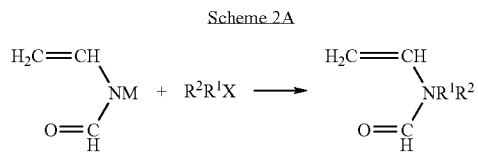

Scheme 2A

In general, M is an alkali metal or alkali earth metal such as potassium or sodium, and X is a halo group (Cl, Br or I). R$^1$ is a spacer group which can be present or absent. R$^1$ is for, example, a C0–C25 alkylene group, a C0–C25 fluroalkylene group or a C0–C25 perfluoro alkylene group. R$^2$ is, for example, H (provided R$^1$ is not absent), an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —OR$^3$, wherein, R$^3$ is an alkyl group, a fluoroalkyl group, a perfluoroalkyl group, or an aryl group, —C(O)R$^4$, —C(O)OR$^4$, —OC(O)R$^4$, wherein R$^4$ is an H, alkyl group, a fluoroalkyl group, a perfluoroalkyl group, or an aryl group, a phthalimide group ($C_6H_4(CO)_2N-$) or NR$^5$R$^6$, wherein R$^5$ and R$^6$ are independently H, —C(O)R$^4$, an alkyl, a fluoroalkyl group, a perfluoroalkyl group or an aryl group.

The syntheses of several N-alkyl-N-vinylformamide compounds, which are representative of the synthetic method of the present invention, is discussed below. The N-alkyl-N-vinylformamide compounds were polymerized to form homopolymers. The homopolymers were hydrolyzed to from derivatized poly(vinylamine). The N-alkyl-N-vinylformamide compounds were copolymerized with NVF and the amphiphilic nature of poly (NVF-co-N-hexyl-N-vinylformamide) was studied. The synthesis of other N-vinylformamide derivatives and polymerization thereof is set forth in the Experimental Examples below.

Synthesis of N-alky-N-vinylformamide Compounds/Monomers

Compounds/Monomers 1a, 1b, 1c and 1d were synthesized by the reaction of N-vinylformamide potassium salt with alkyl bromide. The synthetic procedure included generally two steps as shown in Scheme 2B below. N-vinylformamide potassium salt was prepared by the reaction of N-vinylformamide with potassium t-butoxide in anhydrous tetrahydrofuran under nitrogen atmosphere at a temperature of 10° C. The resulting reaction mixture was a white suspension of N-vinylformamide potassium salt that can be isolated by filtration under nitrogen. In the second step, the monomers can be obtained following two slightly different procedures. One is by the reaction of isolated N-vinylformamide potassium salt with alkyl bromide in anhydrous THF. In the other, the initial reaction mixture is directly used without separation of the potassium salt. It was found that the yield of the monomer was higher by the former procedure (for example, 75% for N-dodecyl-N-vinylformamide 1d by the former procedure as compared to 68% by the latter procedure). In the first step, several other alcoholates or alkoxides (for example, as potassium methoxide or potassium ethanoxide) as well as several other alkali metal hydrides (for example, potassium hydride or sodium hydride) were used without any loss in yield.

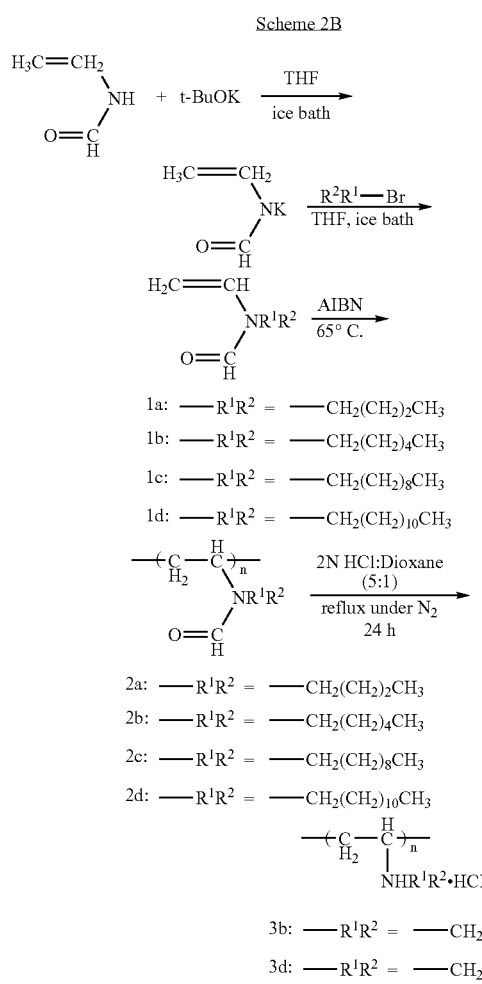

In the second step, the suspension of N-vinylformamide potassium salt in anhydrous THF was maintained at 10° C. during the addition of the alkyl bromide under nitrogen atmosphere. A series of novel monomers such as 1a, 1b, 1c and 1d, differing in the length of alkyl chain, was obtained following Scheme 2B.

The monomers 1a, 1b, 1c and 1d can be isolated and purified, for example, either by distillation or column chromatography over silica gel with diethyl ether/petroleum ether eluent. All four N-alky-N-vinylformamide monomers were yellowish oils and soluble in polar solvents such as methanol, ethanol and non-polar solvents such as petroleum ether.

Figure 2:
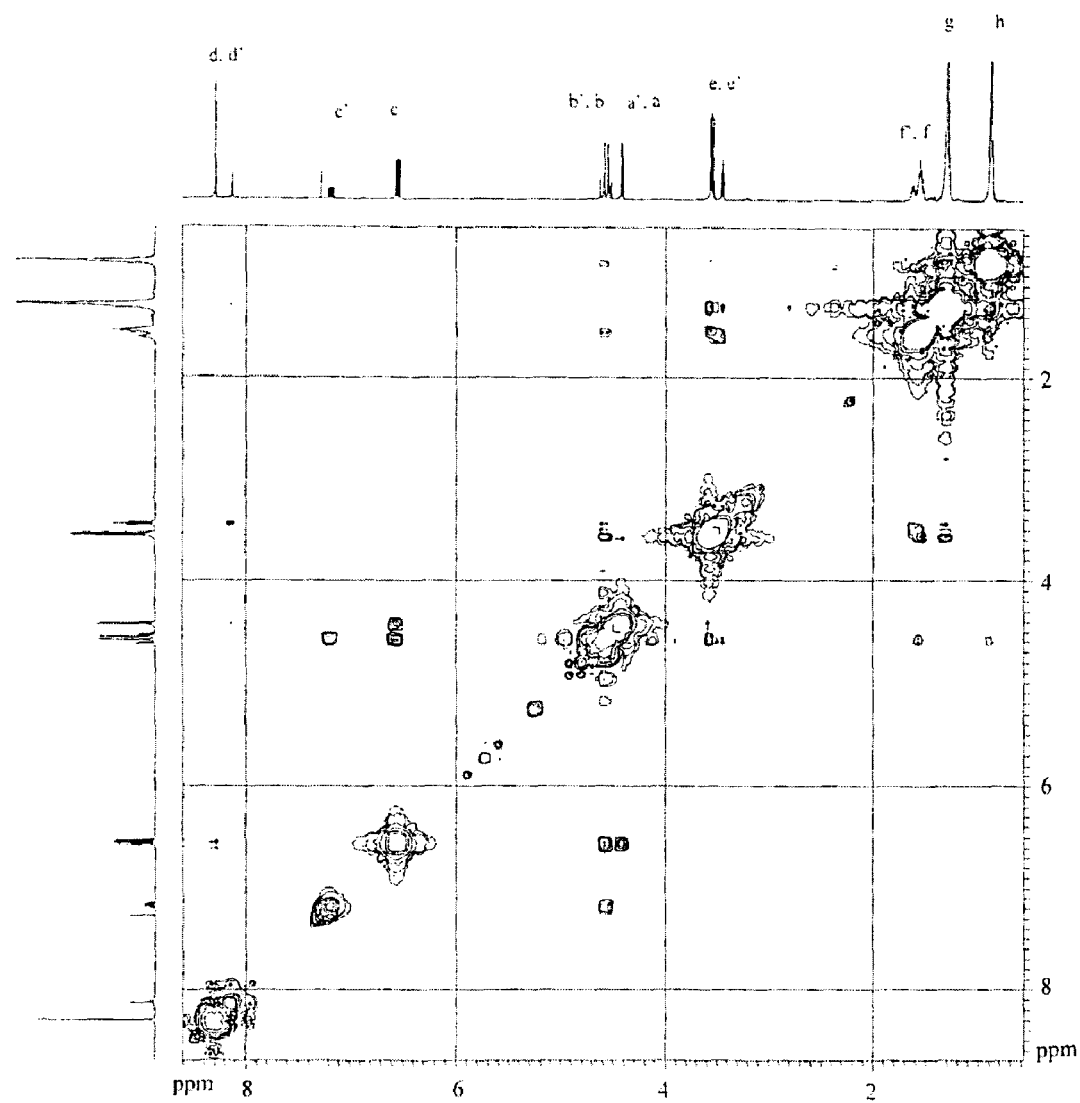
FIG. 2 illustrates a 2D NOE spectrum of N-n-hexyl-N-vinylformamide.

FIG. 1 shows the $^1$H-NMR spectrum of N-n-hexyl-N-vinylformamide, a typical $^1$H-NMR spectrum of N-alkyl-N-vinylformamides of the present invention. It was found that N-n-hexyl-N-vinylformamide, like N-vinylformamide (NVF), is a mixture of two slowly interconverting carbonyl-nitrogen bond rotamers where the ratio of major to minor rotamer is approximately 2.5:1. The ratio of the major rotamer to the minor can be calculated by the ratio of signal intensities of proton on the formyl group at 8.31 ppm (major) and 8.14 (minor). The conformation of the two rotamers was assigned through a 2D NOE experiment (FIG. 2). In FIG. 2, we can see that the $H^d$ at 8.28 and the $H^{d'}$ at 8.1 ppm exhibit a strong cross peak to signals at 6.5 and 3.4 ppm, respectively. Accordingly the aldehyde proton prefers to be cis to the vinyl and not the aliphatic chain.

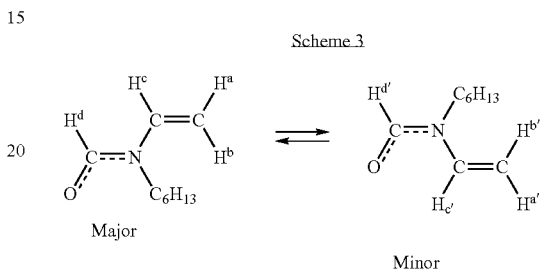

The rotamers were modeled using Macromodel 5.5 and the MM2* force field in chloroform solution. Mohamadi, F.; Richards, N. G.; Guida, W. C.; Liskamp, R.; Lipton, M.; Caulfield, C.; Chang, G.; Hendrickson, T.; Still, W. C. *J. Comput. Chem.* 1990, 11, 440. After simple minimization, the models were refined by using a 1000 step Monte Carlo conformational search, retaining the lowest energy structures. The E rotamer is predicted to be the more stable by 0.38 Kcal/mole which compares well with the NMR value of 0.56 Kcal/mole derived from the equilibrium constant. An examination of the individual energy parameters shows the main difference to be in the electrostatic term, favoring the E rotamer by 0.87 Kcal/mol; indeed, the van der Waals energy term favors the Z isomer slightly (0.21 Kcal/mol). This indicates that the separation of the electron rich vinyl group from the electronegative carbonyl oxygen is the deciding factor in this case. Bourn, et al. in a study of N-methyl and N-ethylformanilides determined that the bulky phenyl group prefers to be trans to the carbonyl oxygen. Bourn, A. J. R.; Gillies, D. G. and Randall, E. W. *Tetrahedron* 1966, 22, 1825. The steric A-value determined from cyclohexyl conformations has the trans alkyl group larger than the vinyl substituent. Bourn, et al. do point out that conjugative effects could be influential. Eliel, E. L.; Wilen, S. H., Mander, L. N. "Stereochemistry of Organic Compounds" Wiley, New York, 1994, pp. 696–697.

Polymerization of N-alky-N-vinylformamides

Polymerizations of N-alky-N-vinylformamide monomers 1a, 1b, 1c and 1d were carried out in bulk in the presence of AIBN at 65° C. The results are summarized in Table 1.

TABLE 1

Bulk polymerization of monomers 1a, 1b, 1c and 1d at 65° C., AIBN as initiator

| polymers | time h | Mn g·mol$^{-1}$ × 10$^{-3}$ | Mw g·mol$^{-1}$ × 10$^{-3}$ | Mw/Mn | conv. % |
|---|---|---|---|---|---|
| 2a | 10 | 13.2 | 27.3 | 2.05 | 86 |
| 2b | 15 | 8.3 | 18.9 | 2.27 | 82 |

TABLE 1-continued

Bulk polymerization of monomers 1a, 1b, 1c and 1d at 65° C., AIBN as initiator

| polymers | time h | Mn g · mol⁻¹ × 10⁻³ | Mw g · mol⁻¹ × 10⁻³ | Mw/Mn | conv. % |
|---|---|---|---|---|---|
| 2c | 15 | 10.0 | 20.4 | 2.05 | 59 |
| 2d | 15 | 10.2 | 21.3 | 2.09 | 56 |
| PNVF | 5 | / | / | / | 70 |

Conversion results as shown in last column in Table 1 demonstrate that all four monomers polymerized, but more slowly than did N-vinylformamide under the same free radical polymerization conditions. In addition, the longer the alkyl chain, the slower the rate of polymerization became. The slower rates of the N-alkyl monomers versus NVF may be attributed to the large alkyl substituent on the nitrogen atom, which may hinder the propagation of the free radicals. Further, the longer the alkyl chain, the larger the steric hindrance, and the polymerization of the monomer becomes more difficult.

The IR spectra of polymers 2a, 2b, 2c and 2d after workup showed that the vinyl absorption bands for the four monomers at 1630 cm⁻¹ had disappeared. Moreover, no signals due to vinyl protons could be seen in their $^1$H-NMR spectra.

All four homopolymers obtained were white powders. Table 2 illustrates the effect of alkyl group chain length on the solubility of the polymers of the present invention by setting forth several solvents and non-solvents for the polymers. The solubility of the polymers depended upon the chain length of alkyl groups in the side chains, where for example, polymer 2a with $(CH_2)_5CH_3$ as side chain is soluble in methanol, but the polymer bearing $—(CH_2)_9CH_3$ in the side chains (thereby making the polymer more nonpolar) is insoluble in methanol and is only soluble in certain low polarity solvents.

TABLE 2

Some solvents and non-solvents for polymers (2a, 2b, 2c and 2d) at room temperature

| polymers | Solvents | non-solvents |
|---|---|---|
| 2a | methanol, THF, acetone, acetonitrile, chloroform, dichloromethane | Water, dioxane, ethyl acetate, benzene, hexane, petroleum ether |
| 2b | methanol, THF, acetone, ethyl acetate, acetonitrile, chloroform, dichloromethane | Water, dioxane, benzene, hexane, petroleum ether |
| 2c | THF, chloroform, dichloromethane, Benzene | Water, methanol dioxane, acetone, acetonitrile, ethyl acetate, hexane, petroleum ether |
| 2d | THF, chloroform, dichloromethane, Benzene | water, methanol dioxane, acetone, acetonitrile, ethyl acetate, hexane, petroleum ether |

Polymer Hydrolysis

Hydrolysis of polymers 2b and 2d were carried out under both acidic and basic conditions. As shown in Table 3, polymer 2b was completely hydrolyzed in 2N—HCl/dioxane mixed solution after refluxing for 24 hours, while polymer 2d was only 60% hydrolyzed under these conditions. It is clear that hydrolytic cleavage of the formyl groups of N-alkylated N-vinylformamide polymers depends on the hydrophobicity of the substituent on the nitrogen atom $[H<CH_2(CH_2)_4CH_3<CH_2(CH_2)_{10}CH_3]$.

TABLE 3

Hydrolysis of polymers 2b and 2d

| polymer | Time H | hydrolysis (%) acidic condition | basic condition |
|---|---|---|---|
| PNVF[12] | 8[12] | 80[12] | 100[12] |
| 2b | 12 | 92 | |
| 2b | 24 | >98 | <10 |
| 2d | 12 | 50 | |
| 2d | 24 | 57 | <10 |

Unexpectedly, both polymers 2b and 2d were not appreciably hydrolyzed in 1 N aqueous NaOH at 80° C. for 24 h. PNVF can be completely hydrolyzed under basic conditions in the present studies (Table 3). See also, Sheehan, J. C. and Yang, D.-D. H. *J. Am. Chem. Soc.* 1958, 80, 1154. Polymer 2b is yellowish powder and soluble in DMF, methanol and hot chloroform. N-alklylated N-vinylformamide polymers depends on the hydrophobicity of the substituent on the nitrogen atom $[H<CH_2(CH_2)_4CH_3<CH_2(CH_2)_{10}CH_3]$. The hydrolysis conditions of the present studies were not optimized. The hydrolysis of each of the polymers of the present invention can be driven to completion.

Figure 3:
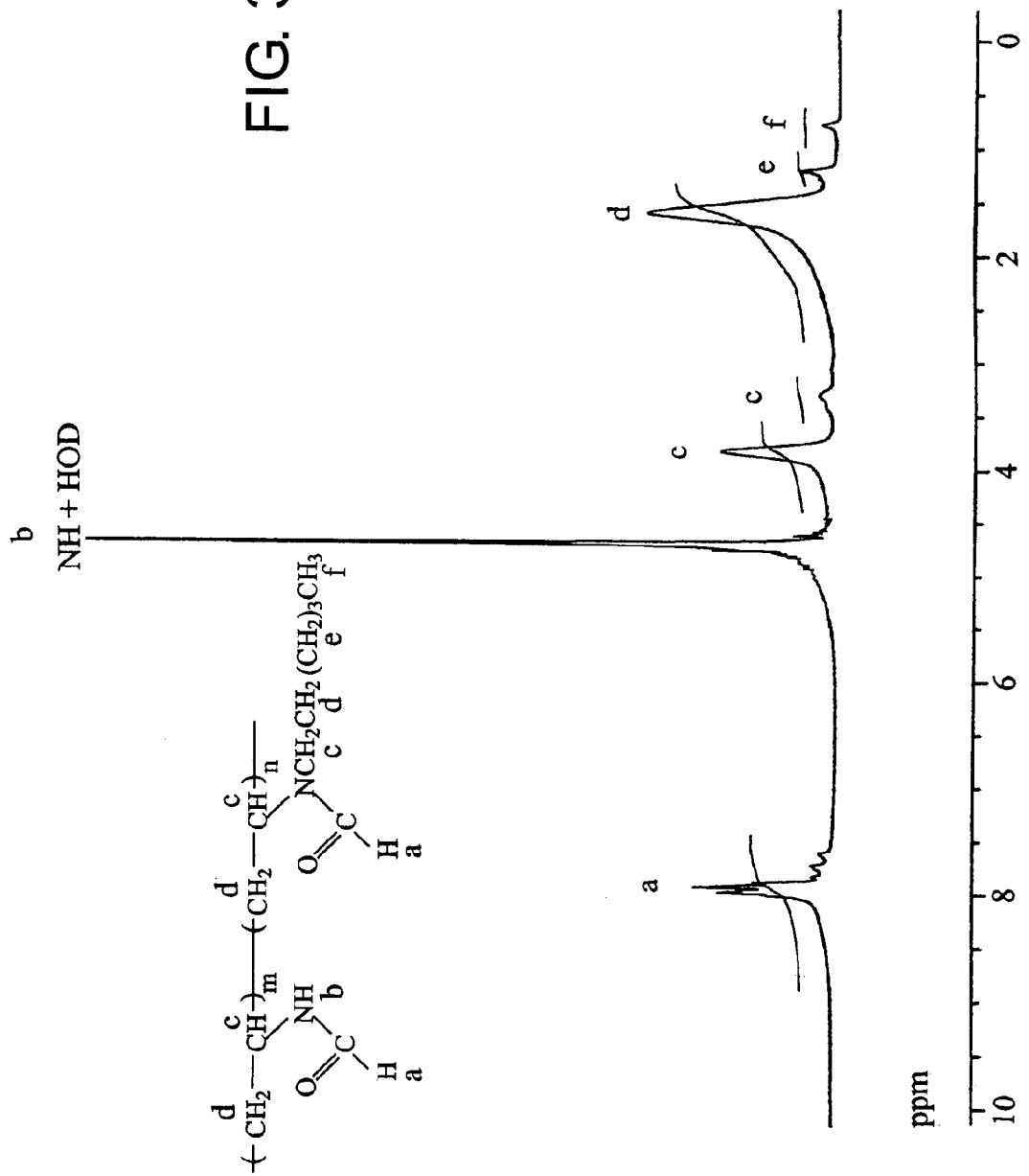
FIG. 3 illustrates an $^1$H-NMR spectrum of poly (NVF-co-N-hexyl-N-vinylformamide).

Characterization of poly (NVF-co-N-hexyl-N-vinylformamide) and its Amphiphilic Properties Copolymers of all four monomers with NVF at several feed ratios were obtained under free radical conditions using AIBN as initiator. FIG. 3 shows the $^1$H-NMR spectrum of poly (NVF-co-N-hexyl-N-vinylformamide). The spectrum confirms the formation of the copolymer with the appearance of both peaks at both 0.81 ppm (—(CH2)₅CH3) and 7.97(—C(═O)H). The copolymer composition were obtained by comparing the peak area of the methyl protons of N-hexyl-N-vinylformamide fragment at 0.81 ppm and the protons of the formyl group of NVF at the 7.97 ppm. The content of N-hexyl-N-vinylformamide in the copolymer was approximately 1.5 mol % when the molar feed ratio of NVF to N-hexyl-N-vinylformamide was 95:5. The copolymer was soluble in water. It was found that when N-hexyl-N-vinylformamide in molar feed ratio was more than 5 mol %, the copolymer was insoluble not only in water but also in most common solvents such as (DMSO, DMF methanol, THF, acetone, ethyl acetate, acetonitrile, chloroform, etc). The solubility of the copolymers in water was also strongly dependent on the alkyl chain length of alkyl NVF. For example, poly (NVF-co-N-dodecyl-N-vinylformamide) only swelled in water even when N-dodecyl-N-vinylformamide was only 5 mol % in the molar feed ratio.

The ability of poly (NVF-co-N-hexyl-N-vinylformamide) to stabilize an oil/water or O/W emulsion was checked by visual inspection. We employed castor oil as the oil phase and water as the dispersed phase. It was found that a homogeneous emulsion were formed using poly (NVF-co-N-hexyl-N-vinylformamide) that was stable for at least 75 min before phase separation appeared. No emulsion can be formed at all with PNVF. Unlike PNVF, the existence of lipophilic hexyl groups on side chains of the polymer of the present invention enables the interaction with the oil phase and the lowering of the interfacial tension with water. Also, poly (NVF-co-N-hexyl-N-vinylformamide) copolymer has a number of graft chains as a result of the relatively high chain transfer constant of PNVF which results in an increase in the molecular adsorption area at the interface. See Gu, L.;

Zhu, S.; Hrymak, A. N.; Pelton, R. H. *Polymer* 2001, 42, 3077–3083; Gu, L.; Zhu, S.; Hrymak, A. N.; Pelton, R. H. *Macromol. Rapid Commun.* 2001, 22, 212–214; Chujo, Y.; Shishino, T.; Tsukahra, Y. and Yamashita, Y. *Polym. J* 1985, 17, 133; Lucas, E. F.; Oliveira, C. M. and Gomes, A. S. *J. Appl. Polym. Sci.* 1992, 46, 733. The mean droplet size of the emulsion measured with dynamic light scattering DLS was 950 nm, a size that is small enough not to block capillaries or lung tissue but large enough not to enter bone marrow, small intestine tissue, or other non-reticuloendothelial system organs. See Buszello, K.; Müller, B. W. in *Pharmaceutical Emulsions and Suspensions*, Nielloud, F. and Marti-Mestres, G., Eds., Marcel Dekker: New York, 2000, Ch. 5, pp. 195–197. Droplet sizes between 123–198 nm have been reported using phosphatidyl choline and mixtures with pegylated phosphatidylethanolamine to emulsify castor oil. Liu, F.; Liu, D. *Int. J. Pharm.* 1995, 125, 73–80. A poly (NVF-co-N-hexyl-N-vinylformamide) emulsion still had some stability even after 7 days.

Qiu and colleagues have examined the preparation of amphiphiles via the functionalization of polyvinyl amine with combinations of hydrophobic and hydrophilic side chains. Qiu, Y.; Zhang, T.; Ruegsegger, M.; Marchant, R. E.; *Macromolecules* 1998, 31, 165–171. In those studies, use of mixed side chains created materials that lower the surface tension of water from 70 dynes/cm to 40 at concentrations of 1.5 mg/ml. The results of those studies suggest that one could create more effective amphiphiles from the N-alkyl functional NVF monomers of the present invention through a copolymerization with an analogous hydrophilically derivatized NVF, such as a PEGylated (wherein PEG is polyethylene glycol) version or another polyether derivatized NVF.

By reacting NVF with a reagent as described above wherein $R^1$ and $R^2$ are fluorinated or fluorous (that is, an organic compound having domains or regions rich in fluorine atoms), compounds suitable for use, for example, as surfactants in fluorous/organic emulsions can be synthesized. Fluorous compounds and fluorous separation techniques are described, for example, in U.S. Pat. Nos. 6,156, 896, 5,859,247 and 5,777,121, and in U.S. patent application Ser. Nos. 09/506,779, 09/565,087, 09/602,105, 09/952,188, 09/877,944 and 10/094,345, assigned to the assignee of the present invention, the disclosure of which are incorporated herein by reference. Such fluorinated surfactants can be hydrolyzed to form the corresponding fluorinated poly (vinylamines). An alternative synthetic route to fluorinated poly (vinylamines) is described in the Experimental Examples below.

Experimental

Materials

N-vinylformamide was donated by the BASF AG and distilled under reduced pressure before use. 1,1'-Azobisisobutyronitrile or AIBN (Aldrich) was recrystallized from ethanol. Potassium methoxide, potassium t-butoxide, potassium hydride, sodium hydride were purchased from Aldrich and used without further purification. Anhydrous THF was purchased from Aldrich. All other solvents were purchased from Aldrich and purified by conventional methods prior to use.

Preparation of N-n-butyl-N-vinylformamide (1a)

Into a dry 500 mL three-necked round-bottomed flask equipped with magnetic stirring bar and dropping funnel were placed 11.67 g (0.164 mol) of N-vinylformamide and 200 mL of anhydrous THF. The mixture was cooled to 15° C. in an ice bath under nitrogen and a total of 18.8 g (0.167 mol) of t-BuOK was added in three portions with constant stirring over 45 minutes. 1-Bromobutane, 24.5 g (0.179 mol) was then added to the reaction mixture dropwise over 30 minutes. When addition was complete, the reaction was allowed to warm to ambient temperature and stirred overnight. After potassium bromide salt was removed, the reaction mixture was concentrated under reduced pressure and diluted with 200 mL of water. The organic layer was extracted three times with diethyl ether. The combined organic layers were washed twice with water and dried over anhydrous magnesium sulfate. The resulting product was recovered after concentration in vacuum and purification by chromatography on silica (diethyl ether/petroleum ether (v/v=3:7). yield: 11.7 g (56%). IR (NaCl, v: cm$^{-1}$): 1693 (—NHC(=O)H); 1630 (C=C). $^1$H-NMR (CDCl$_3$, δ: ppm): 8.31, 8.14 (2s, 1H, —C(=O)H); 7.25–7.16, 6.61–6.52 (m, 1H, H$_2$C=CH—); 4.62–4.45 (m, 1H, H$_a$H$_b$C=CH—); 4.43–(s, 1H, H$_a$H$_b$C=CH—); 3.60–3.45 (t, 2H, —NCH$_2$CH$_2$—); 1.61–1.54 (m, 2H, —CH$_2$CH$_2$CH$_2$—); 1.40–1.32 (m, 2H, —CH$_2$CH$_2$CH$_3$); 0.99–0.94 (t, 3H, —NCH$_2$CH$_2$CH$_2$CH$_3$).

Preparation of N-hexyl-N-vinylformamide (1b)

The synthetic procedure was identical to that described for the preparation of 1a, where 1-bromohexane is used in place of 1-bromobutane. Yield: 63%; IR (NaCl, v: cm$^{-1}$): 1698 (—NHC(=O)H); 1630 (C=C); $^1$H-NMR (CDCl$_3$, δ: ppm): 8.31, 8.14 (2s, 1H, —C(=O)H); 7.25–7.16, 6.61–6.52 (m, 1H, H$_2$C=CH—); 4.65–4.54 (m, 1H, H$_a$H$_b$C=CH—); 4.45–4.42 (s, 1H, H$_a$H$_b$C=CH—); 3.60–3.44 (t, 2H, —NCH$_2$CH$_2$—); 1.65–1.56 (m, 2H, —CH$_2$CH$_2$CH$_2$—); 1.31 (m, 6H, —CH$_2$(CH$_2$)$_3$CH$_3$); 0.90–0.88 (t, 3H, —NCH$_2$(CH$_2$)$_3$CH$_3$).

Preparation of N-decyl-N-vinylformamide (1c)

Into a dry 500 mL three-necked round-bottomed flask was placed 13.8 g (0.194 mol) of N-vinylformamide and 200 mL of anhydrous THF. The mixture was cooled to 4° C. in an ice bath under nitrogen and a total of 22.2 g (0.197 mol) of t-BuOK was added in three portions with constant stirring for 1 hour. The N-vinylformamide potassium salt was filtered, washed with anhydrous diethyl ether and dried under nitrogen. Yield was 92%.

Into a dry 250 mL three-necked round-bottomed flask equipped with magnetic stirring bar and dropping funnel was placed 8 g (0.07 mol) of fresh N-vinylformamide potassium salt and 200 mL of anhydrous THF. 1-Bromodecane, 16.1 g (0.07 mol) was added to the reaction mixture dropwise at 10° C. over 30 minutes. When addition was complete, the reaction was allowed to stir overnight at ambient temperature. The reaction mixture was concentrated under reduced pressure to remove most of the solvent and diluted with 100 mL of water. The organic layer was extracted with diethyl ether. The combined organic layers were washed twice with water and dried over anhydrous magnesium sulfate. The product was recovered after concentration in vacuum and purification by chromatography on silica (diethyl ether/petroleum ether (v/v=2:8). Yield: 13.2 g (89%). IR (NaCl, v: cm$^{-1}$):1702 (—NHC(=O)H); 1631 (C=C); $^1$H-NMR (CDCl$_3$, δ: ppm): 8.43, 8.27 (2s, 1H, —C(=O)H); 7.37–7.28, 6.73–6.65 (m, 1H, H$_2$C=CH—); 4.78–4.67 (m, 1H, H$_a$H$_b$C=CH—); 4.58–4.55 (d, 1H, H$_a$H$_b$C=CH—); 3.72–3.56 (t, 2H, —NCH$_2$CH$_2$—); 1.76–1.62 (m, 2H, —NCH$_2$CH$_2$(CH$_2$)$_7$CH$_3$); 1.44–1.28 (m, 14H, —NCH$_2$CH$_2$(CH$_2$)$_7$CH$_3$); 1.04–1.00 (t, 3H, —NCH$_2$CH$_2$(CH$_2$)$_7$CH$_3$).

Preparation of N-dodecyl-N-vinylformamide (1d)

The synthetic procedure was identical to that described for 1c, where 1-bromododecane is employed. Yield 75%; IR (NaCl, v: cm$^{-1}$): 1694 (—NHC(=O)H); 1630 (C=C); $^1$H-NMR (CDCl$_3$, δ: ppm): 8.30, 8.14 (2s, 1H, —C(=O)H); 7.24–7.15, 6.60–6.52 (m, 1H, H$_2$C=CH—); 4.65–4.56 (m, 1H, H$_a$H$_b$C=CH—); 4.45–4.42 (d, 1H, H$_a$H$_b$C=CH—); 3.59–3.43 (t, 2H, —NCH$_2$—); 1.65–1.57 (m, 2H, —CH$_2$(CH$_2$)$_{10}$CH$_3$); 1.27 (s, 20H, —CH$_2$(CH$_2$)$_{10}$CH$_3$); 0.89–0.87 (t, 3H, —CH$_2$CH$_3$).

Polymerization

In a typical procedure, N-hexyl-N-vinylformamide (1.0 g) and initiator AIBN (18 mg, 1.8 wt % relative to the monomer) were added to an ampoule. Before sealing under vacuum, the contents were degassed by three cycles of freeze-pump-thaw under vacuum. The polymerization was carried out in an oil bath at a constant temperature of 65° C. for a given time (Table 1). The polymer obtained was purified with petroleum ether in Soxhlet extraction for 8 h and dried under reduced pressure at 60° C. for 12h. Conversion was determined gravimetrically. The resulting polymers were characterized by IR and $^1$H-NMR spectra.

2a: IR (KBr, v: cm$^{-1}$): 2959, 2872 (—CH$_3$); 1670 (—C=O); $^1$H-NMR (CDCl$_3$, δ: ppm): 8.03(b, —C(=O)H); 4.23, 3.1(b, —H$_2$C—CHN— and —N—CH$_2$CH$_2$—); 2.0, 1.53 (b, —H$_2$C—CHN— and —N—CH$_2$CH$_2$—); 1.31(s, —CH$_2$CH$_3$); 0.95(s, —CH$_2$CH$_3$).

2b: IR (KBr, v: cm$^{-1}$): 2957(—CH$_3$); 1671 (—C=O); $^1$H-NMR (CDCl$_3$, δ: ppm): 8.03(b, —C(=O)H); 4.23, 3.1 (b, —H$_2$C—CHN— and —N—CH$_2$CH$_2$—); 2.0, 1.53 (b, —H$_2$C—CHN— and —N—CH$_2$CH$_2$—); 1.31(s, —(CH$_2$)$_3$CH$_3$); 0.91(s, —CH$_2$CH$_3$).

2c: IR (KBr, v: cm$^{-1}$): 2955(—CH$_3$); 1673 (—C=O); $^1$H-NMR (CDCl$_3$, δ: ppm): 8.03(b, —C(=O)H); 4.23, 3.1 (b, —H$_2$C—CHN— and —N—CH$_2$CH$_2$—); 2.0, 1.53 (b, —H$_2$C—CHN— and —N—CH$_2$CH$_2$—); 1.27(s, —(CH$_2$)$_7$CH$_3$); 0.89(s, —CH$_2$CH3).

2d: IR (KBr, v: cm$^{-1}$): 2959(—CH$_3$); 1674 (—C=O); $^1$H-NMR (CDCl$_3$, δ: ppm): 8.03(b, —C(=O)H); 4.23, 3.1 (b, —H$_2$C—CHN— and —N—CH$_2$CH$_2$—); 2.0, 1.53 (b, —H$_2$C—CHN— and —N—CH$_2$CH$_2$—); 1.27 (s, —(CH$_2$)$_9$CH$_3$); 0.89 (t, —CH$_2$CH$_3$).

PNVF was prepared by the same procedures as mentioned above: NVF (1.0 g) and initiator AIBN (18 mg, 1.8 wt % relative to the monomer). The polymerization time was 5 h. The polymer obtained was purified with acetone in Soxhlet extraction for 8 h and dried under reduced pressure at 60° C. for 12 h. Conversion was determined gravimetrically.

Polymer Hydrolysis

The hydrolysis of polymers 2b and 2d was carried out under both acidic and basic conditions. Typically, poly(N-n-hexyl-N-vinylformamide) (0.25 g), hydrochloric acid (2N, 10 mL), and dioxane (2 mL) were stirred under reflux or in NaOH (1N, 10 mL) at 80° C. under a N$_2$ atmosphere for a given time (see Table 3). Hydrolysis conditions are described, for example, in Sheehan, J. C. and Yang, D.-D. H. *J. Am. Chem. Soc.* 1958, 80, 1154 and in Pinschmidt, Jr. R. K.; Renz, W. L.; Carrol, W. E.; Yacoub, K.; Drescher, J.; Nordquist, A. F.; Chen, N. *J Macromol. Sci. Pure Appl. Chem.* 1997, A34, 1885. The hydrolyzed polymer was recovered by filtering the suspension and washing with deionized water (50×3 mL). The resulting polymer was dried under reduced pressure at 60° C. for 12 h.

Preparation of N-[2-(N-vinylformamidoethyl)]phthalimide (Scheme 3)

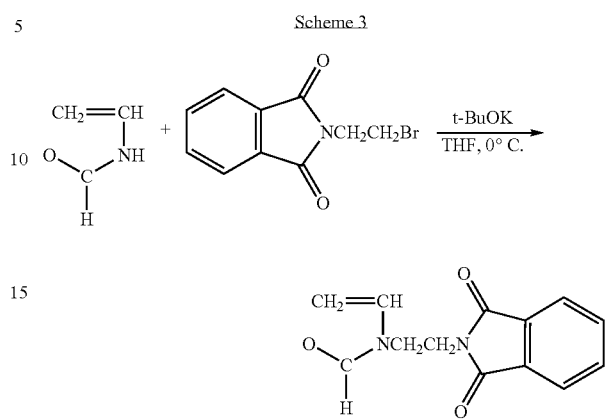

The product is purified by chromatography on silica with benzene as eluent (R$_f$=0.33). The product is a white crystal.

IR (KBr, v: cm$^{-1}$): 1765; 1710; 1636; 1605

$^1$H-NMR (CDCl$_3$, δ: ppm): 7.91–7.87(m, 2H,

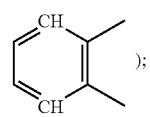);

7.79–7.74 (m, 2H,

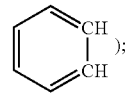);

6.95–6.85 (m,1H, H$_a$H$_b$C=CH—); 6.14 (d, 1H, H$_a$H$_b$C=CH—); 5.09 (d, H$_a$H$_b$C=CH—); 4.13 (t, 2H, —NCH$_2$CH$_2$—); 3.63 (t, 2H, —NCH$_2$CH$_2$N—)

Preparation of Poly(N-[2-(N-vinylformamidoethyl)]phthalimide) and Hydrolysis of the Polymer (Scheme 4)

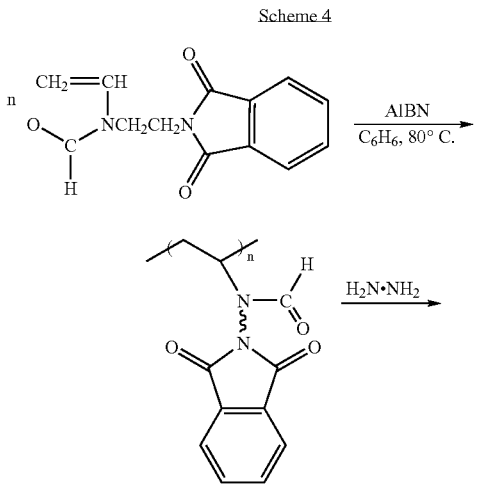

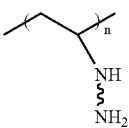

Poly(N-[2-(N-vinylformamidoethyl)]phthalimide) is a white powder, soluble in DMF, insoluble in THF, DMSO, chloroform, benzene, ethanol. The last step of this work is underway.

IR (KBr, v: cm$^{-1}$): 1778; 1707; 1611

Preparation of an Unsaturated Monomer t-Butyl 2-(N-vinylformamido) Acetate and its Related Homopolymers Preparation of an Unsaturated Monomer t-Butyl 2-(N-vinylformamido) Acetate (Scheme 5)

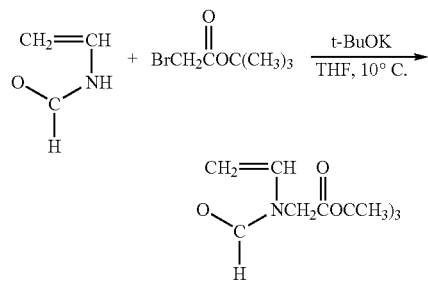

The product is purified by chromatography on silica with diethyl ether/petroleum ether (50/50) as eluent ($R_f$=0.44). The product is a white crystal.

IR (KBr, v: cm$^{-1}$): 1752 (—CH$_2$C(=O)—); 1703 (—N(C=O)H); 1636 (C=C)

$^1$H-NMR (CDCl$_3$, δ: ppm): 8.40, 8.12(s, H, —NC(=OH); 7.32–7.23, 6.73–6.65(m, H, H$_a$H$_b$C=CH—); 4.56–4.42(d, 2H, H$_2$C=CH—); 4.23, 4.04 (s, 2H, —NCH$_2$C(=O)—); 1.44(S, 9H, —OC(CH$_3$)$_3$)

Preparation of Poly(t-Butyl 2-(N-vinylformamido) acetate) and Hydrolysis of the Polymer (Scheme 6)

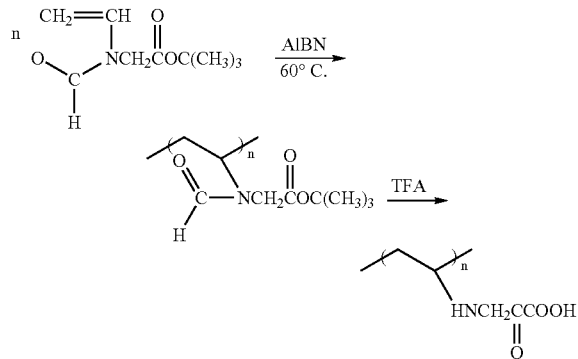

Preparation of poly (NVF-co-N-hexyl-N-vinylformamide)

N-vinylformamide (1.35 g, 19 mmol), N-hexyl-N-vinylformamide (0.16 g, 1 mmol) and AIBN (15 mg) were placed into an ampoule. Before sealing under vacuum, the contents were degassed by three cycles of freeze-pump-thaw under vacuum. The polymerization was carried out in an oil bath at a constant temperature of 60° C. for 3 h. The copolymer was precipitated from petroleum ether and then purified with petroleum ether in Soxhlet extraction for 8 h and dried under reduced pressure at 60° C. for 12 h. Yield was 0.79 g.

Emulsion Preparation

Emulsions were prepared by mixing castor oil (1.6 g), copolymer (0.1 g) or PNVF and deionized water (15 g) in a vial and mixed with a Tissue-Tearor™ (Biospec Products, INC, Model 985370, variable speed from 5,000 to 30,000 PRM) at 30,000 rpm for 5 min at room temperature. The emulsions were characterized by visual inspection of stability and measurement of the oil droplet size.

Alternative Synthesis of Fluorinated Poly(Vinylamine) (PVAm) (see Scheme 7 Below)

Into a dry 250 mL three-necked round-bottomed flask equipped with magnetic stirring bar and dropping funnel were placed 6.65 g (58 mmol) of N-hydroxysuccinimide and 100 mL of anhydrous dimethoxyethane. The mixture was cooled to 0° C. in an ice bath. Pentadecafluorooctanoyl chloride (25 g, 58 mmol) in 25 mL of anhydrous dimethoxyethane was added dropwise to the reaction mixture over 30 minutes. When addition is complete, 5.84 g of triethylamine in 25 mL of anhydrous dimethoxyethane was added dropwise to the reaction mixture and stirred at room temperature for 5 h and then at 50° C. for 1 h. The hot reaction mixture was filtered to remove the salt. The product was obtained by crystallization from the filtrate in a freezer for 30 min. The yield is 16.6 g (56%).

$^1$H-NMR (CDC3, δ: ppm): 3.01(m, 4H)

IR (KBr, v: cm$^{-1}$): 1840 (—C(=O)CF$_2$—); 1710–1780 (—NC(=O)—), 1240, 1206 (—CF$_2$—)

Preparation of Fluorinated PVAm

To a solution of 1 g of PVAm in 20 mL methanol was added 1.75 g of N-hydroxysuccinimide ester of perfluorooctanoic acid in 5 mL methanol. The solution allowed stirring overnight at room temperature. The product was recovered by precipitation from 100 mL 1% aqueous solution of sodium bicarbonate. The product was washed with acetone and water respectively three times and dried under vacuum at 60° C. The yield was 1.8 g.

IR (KBr, v: cm$^{-1}$): 1708 (—C(=O)CF$_2$—); 1240, 1206 (—CF$_2$—); 3292 (—NH$_2$)

Preparation of N-Fluorinated PVAm by the Reduction of Amide Carbonyl Groups in Polymer To the suspension of 1 g of PVAm in 10 mL THF was added dropwise 100 mL of 1M borane in THF in ice bath. After addition was completed, the solution was allowed to stir at 60° C. for 48 h. The solution was permitted to cool to room temperature and 100 ml of 37% hydrochloric acid were added slowly through a dropping funnel. The THF was removed by distillation at atmospheric pressure. Then sodium hydroxide pellets were added. The product was washed with water three times and dried under vacuum at 60° C. the yield was 0.8 g. IR spectrum showed that the peak at 1708 cm$^{-1}$ disappeared. All carbonyl groups were reduced.]

IR (KBr, v: cm$^{-1}$): 1244, 1203 (—CF$_2$—); 3200–3500, 1608 (—NH$_2$)

19

Scheme 7

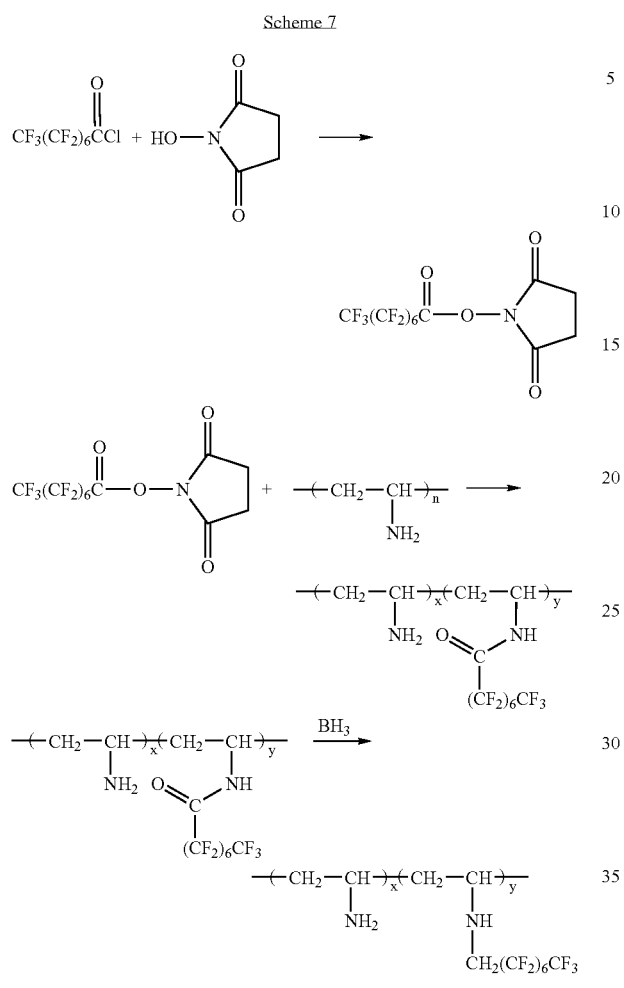

Measurements

IR spectra were recorded on a Nicolet 360 FT-IR spectrometer. NMR experiments were performed on a Bruker AMX500 spectrometer, using CDCl$_3$ as solvent for monomers and polymers and tetramethylsilane as internal standard. The molecular weight was determined with GPC: two narrow-bore Phenogel columns (Linear pore size, 5 μl and 500 Å, Phenomenex) in series maintained at 35° C., equipped with a waters 510 programmable HPLC pump, a Waters 410 differential refractometer maintained at 40° C., and a Waters 745 data module. Molecular weights are relative to monodisperse polystyrene standards (Waters). The solvent used was THF. The extent of polymer hydrolysis in the hydrolytic experiments was determined by a comparison of signal intensities of the proton on formyl group (7.9–8.1 ppm) and the signal intensities of side-chain methyl protons at 0.9 ppm. Emulsion droplet size was measured by dynamic light scattering (Brookhaven Instruments Corporation: 90 Plus Particle Sizer and 90 Plus Particle Sizing Software) immediately after preparation.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A method of synthesizing a compound having the formula:

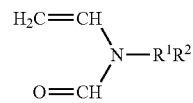

comprising the step of:

reacting a N-vinylformamide salt having the formula

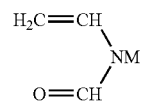

with a compound having the formula XR$^1$R$^2$; wherein X is Br, Cl or I, M is an alkali metal or an alkali earth metal, R$^1$ is a C0–C25 alkylene group, a C0–C25 fluroalkylene group or a C0–C25 perfluoro alkylene group, R$^2$ is H, provided R$^1$ is not absent, an alkyl group, a fluroalkyl group, a perfluoroalkyl group, an aryl group, a hydroxy group, a polyether group, a heterocyclic group of 5 or 6 atoms wherein at least one of the atoms is not a carbon and is N, O, or S, —OR$^3$, wherein, R$^3$ is an alkyl group, a fluoroalkyl group, a perfluoroalkyl group, or an aryl group, —C(O)R$^4$, —C(O)OR$^4$, —OC(O)R$^4$, wherein R$^4$ is an H, an alkyl group, a fluoroalkyl group, a perfluoroalkyl group, or an aryl group, a phthalimide group or NR$^5$R$^5$ wherein R$^5$ and R$^5$ are independently H, —C(O)R$^4$, an alkyl, a fluoroalkyl group, a perfluoroalkyl group or an aryl group.

2. The method of claim 1 wherein the N-vinylformamide salt is formed by reacting an alkali metal base or an alkali earth metal base with N-vinylformamide.

3. The method of claim 2 wherein the alkali metal base is t-BuOK and the N-vinylformamide salt is N-vinylformamide potassium salt.

4. The method of claim 1 wherein X is Br.

5. The method of claim 1 wherein R$^1$ is a C1–C10 alkylene group.

6. The method of claim 1 wherein R$^2$ is a C1–C10 alkyl group.

7. The method of claim 1 wherein R$^1$ is a C1–C10 perfluoroalkylene group.

8. The method of claim 1 wherein R$^2$ is a C1–C10 perfluoroalkyl group.

9. The method of claim 1 wherein R$^2$ is a phthalimide group.

10. The method of claim 1 wherein M is K or Na.

* * * * *